United States Patent
Qian et al.

(10) Patent No.: US 9,101,547 B2
(45) Date of Patent: Aug. 11, 2015

(54) ENTERIC-COATED CAPSULE CONTAINING CATIONIC NANOPARTICLES FOR ORAL INSULIN DELIVERY

(75) Inventors: Yu Qian, Hong Kong (HK); Li Juan Zhang, Hong Kong (HK); Zhi Min Wu, Hong Kong (HK); Li Ying Zhou, Hong Kong (HK); Wei Jiang, Hong Kong (HK); Li Ling, Hong Kong (HK); Qian Luo, Hong Kong (HK); Xin Dong Guo, Hong Kong (HK)

(73) Assignee: NANO AND ADVANCED MATERIALS INSTITUTE LIMITED, Hong Kong (HK)

( * ) Notice: Subject to any disclaimer, the term of this patent is extended or adjusted under 35 U.S.C. 154(b) by 92 days.

(21) Appl. No.: 13/561,105

(22) Filed: Jul. 30, 2012

(65) Prior Publication Data

US 2013/0034602 A1    Feb. 7, 2013

Related U.S. Application Data

(60) Provisional application No. 61/573,014, filed on Aug. 4, 2011.

(51) Int. Cl.

| | |
|---|---|
| *A61K 9/50* | (2006.01) |
| *A61K 38/28* | (2006.01) |
| *A61K 9/16* | (2006.01) |
| *A61K 9/48* | (2006.01) |
| *B82Y 5/00* | (2011.01) |

(52) U.S. Cl.

CPC ............. *A61K 9/5026* (2013.01); *A61K 9/1635* (2013.01); *A61K 9/1647* (2013.01); *A61K 38/28* (2013.01); *A61K 9/4891* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 4,849,227 A * | 7/1989 | Cho .............................. | 424/498 |
| 7,576,067 B2 * | 8/2009 | Weinbach et al. .......... | 514/44 R |
| 7,871,988 B1 | 1/2011 | Sung et al. | |
| 2005/0013866 A1 * | 1/2005 | Maincent et al. ............. | 424/489 |
| 2008/0113031 A1 * | 5/2008 | Moodley et al. .............. | 424/490 |
| 2008/0311182 A1 | 12/2008 | Ferrari et al. | |
| 2010/0021549 A1 | 1/2010 | Meyrueix et al. | |
| 2011/0142927 A1 * | 6/2011 | Sung et al. .................... | 424/463 |
| 2012/0009267 A1 * | 1/2012 | Cho et al. ....................... | 424/497 |

FOREIGN PATENT DOCUMENTS

WO      WO2010113177 A2   10/2010

OTHER PUBLICATIONS

Omathanu Pillai and Ramesh Panchagnula, "Insulin therapies—past, present and future", DDT vol. 6, No. 20 Oct. 2001.
Congrong Lin, Rajeev Gokhale, Jay S. Trivedi, and Vasant Ranade, "Recent Strategies and Methods for Improving Insulin Delivery", Drug Development Research 63:151-160 (2004).
Vikas Agarwal and Mansoor A. Khan, "Current Status of the Oral Delivery of Insulin", Pharmaceutical Technology Oct. 2001: 76-80.
Tin Wui Wong, "Design of oral insulin delivery systems", Journal of Drug Targeting, 2010; 18(2): 79-92.
Brian R. Stoll, Harry R. Leipold, Sam Milstein, David A. Edwards, "A mechanistic analysis of carrier-mediated oral delivery of protein therapeutics", Journal of Controlled Release 64 (2000) 217-228.
Susan K. Paulson, Margaret B. Vaughn, Susan M. Jessen, Yvette Lawal, Christopher J. Gresk, Bo Yan, Timothy J. Maziasz, Chyung S. Cook, and Aziz Karim, "Pharmacokinetics of Celecoxib after Oral Administration in Dogs and Humans: Effect of Food and Site of Absorption", JPET 297:638-645, 2001.
El-Sayed Khafagy, Mariko Morishita, Yoshinori Onuki, Kozo Takayama, "Current challenges in non-invasive insulin delivery systems: A comparative review", Advanced Drug Delivery Reviews 59 (2007) 1521-1546.
Harish Iyer, Anand Khedkar & Manish Verma, "Oral insulin—a review of current status", Diabetes, Obesity and Metabolism 12: 179-185,2010.
Galindo-Rodriguez SA, Allemann E, Fessi H, Doelker E, "Polymeric nanoparticles for oral delivery of drugs and vaccines: a critical evaluation of in vivo studies", Crit Rev Ther Drug Carrier Syst. 2005; 22(5): 419-64.
Yunhui Wu, Alice Loper, Elizabeth Landis, Lisa Hettrick, Linda Novak, Kari Lynn, Cindy Chen, Karen Thompson, Ray Higgins, Udit Batra, Suhas Shelukar, Gloria Kwei, David Storey, "The role of biopharmaceutics in the development of a clinical nanoparticle formulation of MK-0869: a Beagle dog model predicts improved bioavailability and diminished food effect on absorption in human", International Journal of Pharmaceutics 285 (2004) 135-146.
Filippos Kesisoglou, Santipharp Panmai, Yunhui Wu, "Nanosizing—Oral formulation development and biopharmaceutical evaluation", Advanced Drug Delivery Reviews 59 (2007) 631-644.
Christiane Damgé, Catarina Pinto Reis & Philippe Maincent, "Nanoparticle strategies for the oral delivery of insulin", Expert Opin. Drug Deliv. (2008) 5(1): 45-68.
Camile B. Woitiski, Rui A. Carvalho, Antonio J. Ribeiro, Ronald J. Neufeld and Francisco Veiga, "Strategies Toward the Improved Oral Delivery of Insulin Nanoparticles via Gastrointestinal Uptake and Translocation", Biodrugs 2008; 22 (4): 223-237.

(Continued)

*Primary Examiner* — Susan Tran
(74) *Attorney, Agent, or Firm* — Ella Cheong Hong Kong; Sam T. Yip (57) ABSTRACT

The invention relates to an enteric-coated capsule containing cationic nanoparticles for oral insulin delivery, in particular to a type of cationic nanoparticle including a polycationic and mucoadhesive polymer and a biodegradable polymer, wherein each of the nanoparticles has positive surface charge and enhanced permeability for paracellular insulin delivery; the enteric-coated capsule further includes a pH-sensitive polymer as the coating. The enteric-coated capsule containing cationic nanoparticles, when being orally administered to a subject, are configured to prevent the acidic degradation of the active substance such as insulin before being released from said cationic nanoparticles to a specific absorption site along the gastrointestinal tract.

17 Claims, 4 Drawing Sheets

(56) References Cited

OTHER PUBLICATIONS

Anne des Rieux, Virginie Fievez, Marie Garinot, Yves-Jacques Schneider, Véronique Préat, "Nanoparticles as potential oral delivery systems of proteins and vaccines: A mechanistic approach", Journal of Controlled Release 116 (2006) 1-27.

11th International Congress on Amino Acids, Peptides and Proteins, Vienna, Austria, Aug. 3-7, 2009.

Yu-Hsin Lin, Kiran Sonaje, Kurt M. Lin, Jyuhn-Huarng Juang, Fwu-Long Mi, Han-Wen Yang, Hsing-Wen Sung, "Multi-ion-crosslinked nanoparticles with pH-responsive characteristics for oral delivery of protein drugs", Journal of Controlled Release 132 (2008) 141-149.

Fu-De Cui, An-Jin Tao, Dong-Mei Cun, Li-Qiang Zhang, Kai Shi, "Preparation of Insulin Loaded PLGA-Hp55 Nanoparticles for Oral Delivery", Journal of Pharmaceutical Sciences, vol. 96, No. 2:421-427.

S. Sajeesh, Chandra P. Sharma, "Novel pH Responsive Polymethacrylic Acid—Chitosan—Polyethylene Glycol Nanoparticles for Oral Peptide Delivery", J Biomed Mater Res B Appl Biomater. Feb. 2006;76(2):298-305.

Catarina Pinto Reisa, Anfonio J. Ribeiro, Simone Houng, Francisco Veiga, Ronald J. Neufeld, "Nanoparticulate delivery system for insulin: Design, characterization and in vitro/in vivo bioactivity", European Journal of Pharmaceutical Sciences 30 (2007) 392-397.

Kiran Sonaje, Yu-Hsin Lin, Jyuhn-Huarng Juang, Shiaw-Pyng Wey, Chiung-Tong Chen, Hsing-Wen Sung, "In vivo evaluation of safety and efficacy of self-assembled nanoparticles for oral insulin delivery", Biomaterials 30 (2009) 2329-2339.

Lichen Yin, Jieying Ding, Chunbai He, Liming Cui, Cui Tang, Chunhua Yin, "Drug permeability and mucoadhesion properties of thiolated trimethyl chitosan nanoparticles in oral insulin delivery", Biomaterials 29 (2009) 5691-700.

Anchalee Jintapattanakit, Varaporn Buraphacheep Junyaprasert, Thomas Kissel, "The Role of Mucoadhesion of Trimethyl Chitosan and PEGylated Trimethyl Chitosan Nanocomplexes in Insulin Uptake", Journal of Pharmaceutical Sciences, vol. 98, No. 12:4818-4830.

Britta Deutel, Melanie Greindl, Michael Thaurer, and Andreas Bernkop-Schnürch, "Novel Insulin Thiomer Nanoparticles: In Vivo Evaluation of an Oral Drug Delivery System", Biomacromolecules 2008,9,278-285.

Anchalee Jintapattanakit, Varaporn B. Junyaprasert, Shirui Maob, Johannes Sitterberg, Udo Bakowsky, Thomas Kissel, "Peroral delivery of insulin using chitosan derivatives: A comparative study of polyelectrolyte nanocomplexes and nanoparticles", International Journal of Pharmaceutics 342 (2007) 240-249.

Kiran Sonaje, Kun-Ju Lin, Shiaw-Pyng Wey, Che-Kuan Lin, Tzyy-Harn Yeh, Ho-Ngoc Nguyen, Chia-Wei Hsu, Tzu-Chen Yen, Jyuhn-Huarng Juang, Hsing-Wen Sung, "Biodistribution, pharmacodynamics and pharmacokinetics of insulin analogues in a rat model: Oral delivery using pH-Responsive nanoparticles vs. subcutaneous injection", Biomaterials 26 (2010) 6849-58.

Kiran Sonaje, Yi-Jia Chen, Hsin-Lung Chen, Shiaw-Pyng Wey, Jyuhn-Huarng Juang, Ho-Ngoc Nguyen, Chia-Wei Hsu, Kun-Ju Lin, Hsing-Wen Sung, "Enteric-coated capsules filled with freeze-dried chitosan/poly(g-glutamic acid) nanoparticles for oral insulin delivery", Biomaterials 31 (2010) 3384-3394.

Andreas Bernkop-Schnürch, "Chitosan and its derivatives: potential excipients for peroral peptide delivery systems", International Journal of Pharmaceutics 194 (2000) 1-13.

Yu-Hsin Lin, Chiung-Tong Chen, Hsiang-Fa Liang, Anandrao R Kulkarni, Po-Wei Lee, Chun-Hung Chen and Hsing-Wen Sung, "Novel nanoparticles for oral insulin delivery via the paracellular pathway", Nanotechnology 18 (2007) 105102.

Mauro Ferrari, "Nanovector therapeutics", Current Opinion in Chemical Biology 2005, 9:343-346.

Cliff Wong, Triantafyllos Stylianopoulos, Jian Cui, John Martin, Vikash P. Chauhan, Wen Jiang, Zoran Popovic, Rakesh K. Jain, Moungi G. Bawendi, and Dai Fukumura, "Multistage nanoparticle delivery system for deep penetration into tumor tissue", Proc Natl Acad Sci U S A. Feb. 8, 2011;108(6):2426-31.

Rita E. Serda, Biana Godin, Elvin Blanco, Ciro Chiappini, Mauro Ferrari, "Multi-stage delivery nano-particle systems for therapeutic applications", Biochimica et Biophysica Acta 1810 (2011) 317-329.

Ennio Tasciotti, Xuewu Liu, Rohan Bhavane, Kevin Plant, Ashley D. Leonard, B. Katherine Price, Mark Ming-Cheng Cheng, Paolo Decuzzi, James M. Tour, Fredika Robertson and Mauro Ferrari, "Mesoporous silicon particles as a multistage delivery system for imaging and therapeutic applications", Nat Nanotechnol. Mar. 2008;3(3):151-7.

* cited by examiner

ENTERIC-COATED CAPSULE CONTAINING CATIONIC NANOPARTICLES FOR ORAL INSULIN DELIVERY

CROSS-REFERENCE TO RELATED APPLICATIONS

The present application claims priority of U.S. provisional application Ser. No. 61/573,014 filed Aug. 4, 2011, the disclosure of which is incorporated herein by reference.

FIELD OF THE INVENTION

The present invention relates to an enteric-coated capsule containing cationic nanoparticles for oral insulin delivery, and more particularly, to an enteric-coated capsule that contains insulin-loaded cationic nanoparticles which include a type of polycationic polymer in each of the nanoparticles to enable a controlled release of insulin. The present invention also relates to methods of preparing cationic nanoparticles and preparing an enteric-coated capsule containing the cationic nanoparticles.

TECHNICAL BACKGROUND

Multiple daily injections of insulin remain the traditional approach for the treatment of insulin-dependent diabetic patients (Drug Discovery Today 2001, 6: 1056-1061). However, suboptimal control of blood glucose level and poor patient compliance are the associated disadvantages with this treatment (Drug Dev Res 2004, 63: 151-160). Oral insulin delivery is a more convenient way to administer insulin to diabetic patients as it is the most physiologically comfortable means (Pharm Technol 2001, 10: 76-90; Journal of Drug Targeting 2010, 18: 79-92). Nevertheless, creating an oral formulation is a daunting task for all bioactive macromolecules, due to the highly organized barriers that the macromolecules encounter in the gastrointestinal (GI) tract, such as rapid enzymatic degradation and the poor intestinal absorption (J Controlled Release 2000, 64: 217-228). In addition, protein drugs that possess narrow absorption windows often exhibit variable exposures leading to their poor drug transportation in the GI tract (J Pharmacol Exp Ther 2001, 297: 638). For many years, various strategies have been developed to enhance oral delivery of insulin (Advanced Drug Delivery Reviews 2007, 59: 1521-1546; Diabetes Obesity & Metabolism 2010, 12: 179-185). Polymeric nanoparticles are of special interest due to the pharmaceutical advantage such as enabling modulation of physicochemical characteristics (Critical reviews in therapeutic drug carrier systems 2005, 22: 419-463). Moreover, their submicron size and their large specific surface area favor their absorption compared to larger carriers (International journal of pharmaceutics 2004, 285: 135-146; Advanced drug delivery reviews 2007, 59: 631-644).

In order to overcome the barriers mentioned above, oral insulin nanoparticles have been widely investigated to increase their biological activity in experimental animals (Expert Opinion on Drug Delivery 2008, 5: 45-68; Biodrugs 2008, 22: 223-237; J Controlled Release 2006, 116: 1-27). The first obstacle for oral delivery of insulin is in the stomach which forms the boundary between the intestine and the external environment. Special pH-sensitivity of nanoparticles provides the protection to confront this first barrier by preventing insulin from contacting the highly acidic medium in the stomach (Amino Acids 2009, 37: 97-97; J Controlled Release 2008, 132: 141-149; J Pharm Sci 2007, 96: 421-427; Journal of Biomedical Materials Research Part B: Applied Biomaterials 2006, 76: 298-305; Eur J Pharm Sci 2007, 30: 392-397; Biomaterials 2009, 30: 2329-2339). The second barrier for oral delivery of insulin is poor intestinal absorption. To overcome this barrier, special mucoadhesive nanoparticles are developed to prolong insulin nanoparticles' intestinal residence time and increase the permeability of mucosal epithelium, thus finally facilitating insulin entering into systemic circulation (Biomaterials 2009, 30: 2329-2339; Biomaterials 2009, 30: 5691-5700; J Pharm Sci 2009, 98: 4818-4830; Biomacromolecules 2008, 9: 278-285; Int J Pharm 2007, 342: 240-249; U.S. Pat. No. 7,871,988 B1). Double-functional nanoparticles with both pH-sensitivity and mucoadhesivity can overcome all the barriers mentioned above (Biomaterials 2010, 31: 6849-6858). Inserting the double-functional nanoparticles into the enteric-coated capsule could protect against the pH instability of nanoparticles in the stomach (Biomaterials 2010, 31: 3384-3394). It has been suggested that the positive charge of insulin nanoparticles is a positive factor for insulin absorption (Int J Pharm 2000, 194: 1-13). The nanoparticles having a more positive charge are more effective on opening tight junctions, leading to an increase in paracellular permeability (Nanotechnology 2007, 18: 1-11). However, a polycationic nanoparticle with mucoadhesivity and pH-sensitivity may be a non-synergistic carrier for insulin, since the positive charge of the polymer in those nanoparticles could reduce the stability of the nanoparticles in the stomach and the pH-sensitivity of the polymer in those nanoparticles could weaken the positive charge of the nanoparticles in the intestine (Biomaterials 2009, 30: 2329-2339).

Fortunately, the GI barriers are sequential in nature; therefore the probability of reaching the therapeutic objective is the contribution of each individual probability to overcome each barrier (Current opinion in chemical biology 2005, 9: 343-346). The multistage delivery system has a separate intended function, which can efficiently overcome various barriers and simultaneous delivery of independent systems (Proceedings of the National Academy of Sciences 2011, 108: 2426; Biochimica et Biophysica Acta 2011; Nature nanotechnology 2008, 3: 151-157; U.S. Pat. Pub. No. 2008/0311182 A1).

Thus, a two-stage delivery system is needed for allowing a high degree of selectivity in the stage 1 enteric capsule and in the stage 2 cationic nanoparticles Such a two-stage deliver system would have an excellent synergistic effect together with pH-sensitivity and a mucoadhesive property.

SUMMARY OF THE INVENTION

It is one object of the present invention to provide an enteric-coated capsule containing cationic nanoparticles for oral delivery of insulin. The enteric-coated capsule is sensitive to pH change, and can therefore dissolve rapidly in the upper region of the small intestine and release the cationic nanoparticles sequentially. The cationic nanoparticles of the present invention are configured to open the tight junction in the small intestine and enhance the absorption of released insulin.

In an exemplary embodiment, each of the cationic nanoparticles comprises a polycationic polymer, a biodegradable polymer, an insulin molecule and a stabilizer. In one embodiment, the polycationic polymer employed is Eudragit® RS (RS), which is a copolymer of acrylic and methacrylic acid esters, with molecular weight range of 150 to 200 kDa; the biodegradable polymer is poly(lactic acid-co-glycolic acid) (PLGA) with molecular weight range of 20 to 40 kDa; the stabilizer is polyvinyl alcohol; and the insulin molecule is selected from the group consisting of regular insulin and insulin analog. In one embodiment, the enteric-coated capsule comprises a hard gelatin capsule, a pH-sensitive coating layer, the cationic nanoparticles, and a solubilizer, wherein the pH-sensitive coating layer is selected from the group consisting of hydroxypropylmethylcellulose phthalate, hydroxypropylmethylcellulose acetate succinate, ethyl acrylate and methyl methacrylate, such as HP55 and RL100.

The second object of the present invention relates to a method of preparing cationic nanoparticles contained in an enteric-coated capsule. In one embodiment, the method of preparing cationic nanoparticles includes forming an inner water phase comprising the insulin solution at a concentration range of 5 to 10 mg/mL; forming an oil phase comprising the dichloromethane solution of RS and PLGA at a concentration range of 20 to 50 mg/mL; forming an external aqueous phase comprising the polyvinyl alcohol (PVA) solution at a concentration range of 1 to 10 mg/mL as a stabilizer; forming a primary emulsion comprising the inner water phase at a volume of 0.5 to 1 mL and the oil phase at a volume of 3 to 5 mL, wherein the primary emulsion is formed by ultrasonic for a time range of 30 to 60 s at a power range of 40 to 60 w; forming a double emulsion comprising the primary emulsion at a volume of 3.5 to 6 mL and the external aqueous phase at a volume of 20 to 40 mL, wherein the double emulsion formed by ultrasonic for a time range of 60 to 120 s at a power range of 40 to 60 w; forming an insulin-loaded PLGA/RS nanoparticles by evaporation the dichloromethane from the double emulsions; forming a purified insulin-loaded PLGA/RS nanoparticles by centrifugation and water washing of the PLGA/RS nanoparticles three times; forming the cationic nanoparticles by freeze-drying the purified insulin-loaded PLGA/RS nanoparticles. The freeze-dried nanoparticles are ready for encapsulation in an enteric-coated capsule or any pharmaceutically acceptable carrier for oral insulin delivery in a controlled release manner.

The third object of the present invention relates to a method of preparing an enteric-coated capsule containing the cationic nanoparticles of the present invention for oral insulin delivery. In one embodiment, the method includes providing an empty capsule; providing the cationic nanoparticles, wherein each of the nanoparticles comprises RS, PLGA, and at least one bioactive agent; filling the cationic nanoparticles into the empty capsule, wherein the amount of cationic nanoparticles at a dosage of 50 IU/kg; coating the HP55 (or optionally RL100) polymer on the surface of capsule, wherein forming HP55 layer further comprises preparing the dichloromethane and acetone solution of HP55 at a concentration range of 40 to 80 mg/mL.

DEFINITION

I. Insulin

The term "insulin", as used herein, refers to any naturally occurring or recombinant insulin, for example, insulin analogs and derivatives. Insulin from any suitable species can be used, such as human, pig, cow, dog, sheep. In a preferred embodiment, the insulin is porcine insulin. "Regular insulin" as disclosed herein may refer to naturally-occurring insulin or synthetic insulin molecule. Naturally-occurring insulin or synthetic insulin molecule may include, but not limited to, monomeric, polymeric and/or fibril-like insulin, and different forms of insulin molecule depends on different pH values.

Porcine insulin is a two chain, glycosylated polypeptide chain containing 51 amino acids and having a molecular mass of 5,777 Dalton. The alpha and beta chains are joined by two interchain disulfide bonds. The alpha chain contains an intrachain disulfide bond. Insulin regulates the cellular uptake, utilization, and storage of glucose, amino acids, and fatty acids and inhibits the breakdown of glycogen, protein, and fat. Insulin having various degrees of biological activity is commercially available. For instance, it is possible to purchase low-, intermediate-, and rapid-acting forms of insulin. In a preferred embodiment, the biological activity range of porcine insulin is 27 to 28 IU/mg.

II. Cationic Nanoparticles

As used herein, the term "cationic nanoparticles" refers to particles having a diameter of preferably around 250-400 nanometers, typically about 250-300 nanometers and having a positive surface potential around +30 mV-40 mV. Cationic nanoparticles have many properties including but not limited to a mucoadhesive property and an ability to release insulin in a controlled release manner when administered to a subject as a capsule or in another pharmaceutically acceptable carrier containing the cationic nanoparticles.

Cationic nanoparticles can be made using a variety of biocompatible polymers including those that are well known in the art. Suitable polycationic polymers include, but are not limited to, a copolymer of acrylic and methacrylic acid esters, e.g., Eudragit® RS polymer, having quaternary ammonium cations, which are permanently charged, independent of the pH of their solution. The term "cationic" or "polycationic", as used herein, refers to the positive zeta potential of nanoparticles when suspended in an aqueous solution, which is typically less than +8 mV in pH=7.0 medium and acceptable in the simulated intestinal medium. Cationic nanoparticles may contain blends of polycationic polymer and biodegradable polymers, of different molecular weight and/or weight ratio. Preferred blending polymers include poly(hydroxy acids) compromising polylactic acid, polyglycolic acid, and copolymers, especially poly(lactic acid-co-glycolic acid) (PLGA) that can be degraded by hydrolysis following exposure to the environment of the body.

Formulation of nanoparticles can be achieved by double emulsions solvent evaporation method. Ultrasonic emulsification is used to reduce the size of the polymer/insulin emulsions to less than 500 nanometers, preferably below 300 nanometers.

III. Enteric-Coated Capsule

As used herein, the term "enteric" refers to the capsule coated with a material that permits transition through the stomach to the small intestine before the insulin is released. Examples of enteric coating polymers include hydroxypropylmethylcellulose phthalate (HPMCP), hydroxypropylmethylcellulose acetate succinate (HPMCAS) and RL100, and especially HP-55, which can be easily coated on the capsule and dissolved in the upper intestinal conditions.

DETAILED DESCRIPTION OF THE INVENTION

Example 1

Preparation of Insulin-Loaded Cationic Nanoparticles

The preparation of nanoparticles is carried out by the multiple emulsions technique. Briefly, 1 mL of an aqueous solution of insulin (1 mg/mL) is first emulsified, by sonication at a power of 40 W for 30 s, in methylene chloride (5 mL) containing 100 mg of polymers (PLGA/Eudragit RS, 50/50). The resulting first emulsion is thereafter poured into 40 mL of a polyvinyl alcohol aqueous solution (1%) and sonicated at a power of 60 W for 1 min, involving the formation of the multiple emulsions. After evaporation of methylene chloride under reduced pressure, the nanoparticles are collected and washed three times by centrifugation at 20,000 rpm for 10 minutes. After prefreezing of the resultant dispersion (concentration of nanoparticles and cryoprotectant are 1% and 1.5%, respectively) at −20° C. overnight, this mixture is then subjected to vacuum freeze drying.

TABLE 1

| Trehalose % | Mean particle Size (nm) | PDI | Zeta Potential (mV) |
|---|---|---|---|
| before freeze-drying | 374.6 ± 3.8 | 0.39 ± 0.03 | 37.9 ± 2.2 |
| 0% | Δ | Δ | 11.46 ± 3.9 |
| 0.25% | 1426 ± 277.8 | 0.75 ± 0.27 | 15.85 ± 2.3 |
| 0.5% | 664.6 ± 23.2 | 0.54 ± 0.12 | 30.29 ± 1.8 |
| 1.0% | 483.0 ± 14.1 | 0.42 ± 0.06 | 31.43 ± 1.2 |
| 1.5% | 370.6 ± 4.1 | 0.40 ± 0.01 | 30.39 ± 1.5 |
| 2.0% | 374.7 ± 6.7 | 0.44 ± 0.07 | 31.74 ± 1.3 |

Δ: Precipitation/Aggregation of nanoparticles is observed.

The size and zeta potential of test nanoparticles before/after freeze-drying in the presence of different concentrations of trehalose are investigated and compared as shown in Table 1. Before freeze-drying, each nanoparticle has a mean particle size of 374.6±3.8 nm with a positive zeta potential of 37.9±2.2 mV. After freeze-drying, nanoparticles without the addition of trehalose form macroscopic aggregates, which lead to the size and zeta potential un-measureable by a Zetasizer. At lower trehalose concentration range (<1.0%), with the concentration increasing, the size and polydispersity of nanoparticles are reduced significantly due to the decrease in freezing stress. In addition, no obvious changes in size and polydispersity are observed when the trehalose concentration is equal to or above 1.5%. On the other hand, it has been found that the addition of trehalose to PLGA/RS nanoparticles suspension before freeze-drying decreases the positive surface charge from +37.9 mV to approximately +30 mV. This may be due to the hydrogen bonding between hydroxyl groups of the trehalose and the surface of nanoparticles. At a trehalose concentration below 0.25%, the large aggregation and the reduction of zeta potential are due to the lack of formation of an amorphous matrix that preserves the suspension. It has been proved that trehalose is more effective for stabilizing PLGA/RS nanoparticles during freeze-drying at concentration 1.5% or above.

Example 2

Characterization of Insulin-Loaded Cationic Nanoparticles

Generally, nanoparticles have greater intracellular uptake compared with microparticles, and are available to a greater range of biologic targets due to their smaller size and mobility. Decreasing the nanoparticles size leads to an increased absorption of insulin by intestinal cell. Many formulation and process parameters affecting nanoparticles size are studied in the present invention in the multiple emulsions solvent evaporation method, such as sonication time, polymer amount, surfactant concentration and the volume of oil phase and external aqueous phase, etc. It is believed that varying the volume of external aqueous phase is the easiest way to modulate the size of nanoparticles of the present invention. As shown in Table 2, decreasing the volume of external aqueous phase could decrease the size and increase zeta potential value of nanoparticles. The smaller the volume of external aqueous phase is, the greater the power density of sonication is applied, leading to a smaller mean nanoparticles size. In addition, the increase in polydispersity index (PDI) of nanoparticles may be due to uneven power density distribution of sonication in the larger volume of external aqueous phase.

TABLE 2

| Volume (mL) | LE (%) | Mean particle size (nm) | PDI | Zeta potential (mV) |
|---|---|---|---|---|
| 10 | <20 | 238 ± 3.2 | 0.19 ± 0.08 | 43.7 ± 2.1 |
| 20 | 73.9 | 285.6 ± 4.5 | 0.26 ± 0.09 | 42.9 ± 1.4 |
| 30 | 91.3 | 370.6 ± 4.1 | 0.39 ± 0.11 | 35.5 ± 0.4 |
| 40 | 71 | 387.2 ± 8.8 | 0.4 ± 0.17 | 30.39 ± 1.5 |
| 50 | 60.7 | 420.7 ± 13.2 | 0.38 ± 0.12 | 31.39 ± 3.1 |

Figure 1:
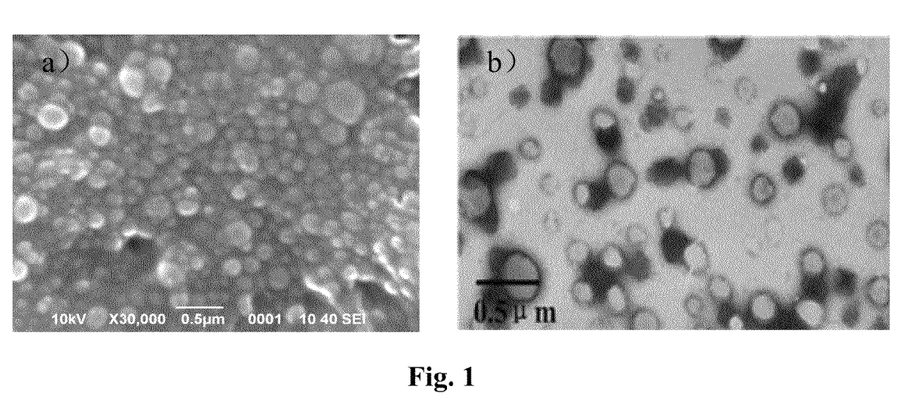
FIG. 1 shows the SEM image of the insulin-loaded cationic nanoparticles.

Each of the prepared PLGA/RS nanoparticles has a mean particle size of 285.6±4.5 nm with a positive zeta potential 42.9±1.4 mV. Their insulin loading efficiency and loading content were 73.9% and 6.7% as shown in Table 2. The morphology of PLGA/RS nanoparticles by SEM and TEM analysis are shown in FIG. 1. The optimized nanoparticles possess a spherical shape and uniform size.

Example 3

Zeta Potential of PLGA/RS Nanoparticles in Different pH Conditions

The zeta potential value is an important particle characteristic as it can influence both nanoparticle stability and mucoadhesion in GI conditions. Mucoadhesion can be promoted by a positive zeta potential value. The mucus layer itself is at a neutral pH value with an anionic polyelectrolyte. Consequently, the presence of positively charged groups on the nanoparticles could lead to electrical charge interactions between the mucus and the particles. As shown in Table 3, the zeta potential value and size of the PLGA/RS nanoparticles have been investigated in the pH range 1.2-7.2, mimicking the GI physiological conditions. It is clear that pH value of medium plays an important role in the zeta potential value of nanoparticles. Generally, the quaternary ammonium cations in RS polymer are permanently charged, independent of the pH of their solution. Insulin (PI=5.4) becomes a positively charged molecule at pH 1.2. Theoretically, the insulin-loaded PLGA/RS nanoparticles would have a higher zeta potential due to the increased positive charge of insulin with an increase in acidity. Nevertheless, the zeta potential of PLGA/RS nanoparticles becomes less positive from pH 2.5 to 1.2. This less positive zeta potential may be attributed to the presence of too much free PVA absorbed on those more positive nanoparticles and a shielding effect of the PVA layer in strong acidic condition. The PVA layer on the surface of nanoparticles prevents the self-aggregation of the nanoparticles and has steric stabilizing effect. This is confirmed by mean particle size of nanoparticles in acidic conditions (e.g. pH<6.0) showing no obvious change. In the case of the simulated intestinal medium of pH>6.0, the zeta potential of PLGA/RS nanoparticles reduces due to the neutralization of the negatively charged insulin as well as increased counter ion, leading to the aggregation of the nanoparticles.

For PLGA/RS nanoparticles, the mucoadhesion would result in remaining of nanoparticles in stomach due to the surface positive charge. In addition, from the higher zeta potential in pH=6.0-6.6 medium than that in pH>6.6, the mucoadhesive property of PLGA/RS nanoparticles may be better in the luminal surface of duodenal (pH 6.0-6.6) than those of jejunum (pH=7.0) and ileum (pH=7.4), thus more nanoparticles should adhere to duodenal than jejunum and ileum. Hence, to reduce the remaining of PLGA/RS nanoparticles in stomach, the enteric-coated capsule is introduced to fill with the freeze-dried nanoparticles in Example 1. In addition, the capsule with the HP55 (pKa=5.5) as the enteric polymer could protect the PLGA/RS nanoparticles adhering in the upper of intestine, allowing the adsorption of insulin for a long period of time.

TABLE 3

| pH value | Mean Particle Size (nm) | PDI | Zeta potential (mV) |
|---|---|---|---|
| 1.2 | 244.3 ± 2.3 | 0.238 ± 0.019 | 18.3 ± 3.7 |
| 2.0 | 246.3 ± 1.2 | 0.285 ± 0.035 | 25.4 ± 4.2 |
| 2.5 | 250.7 ± 2.5 | 0.245 ± 0.020 | 33.9 ± 2.1 |
| 6.0 | 350.2 ± 21.2 | 0.359 ± 0.065 | 32.6 ± 0.5 |
| 6.6 | 393.7 ± 12.2 | 0.409 ± 0.058 | 23.7 ± 0.5 |
| 7.0 | 437.7 ± 19.0 | 0.491 ± 0.019 | 8.6 ± 0.4 |
| 7.2 | 543.2 ± 22.1 | 0.528 ± 0.018 | 7.9 ± 0.1 |

Example 4

In Vitro Insulin Release Study

The enteric polymers HP55 are applied to coat the hard gelatin capsules for the pH-dependent targeted delivery of PLGA/RS nanoparticles in the small intestine. Enteric coating with HP55 enables to withstand prolonged contact with acidic gastric fluids, but readily dissolves in the neutral environment of the small intestine.

Figure 2:
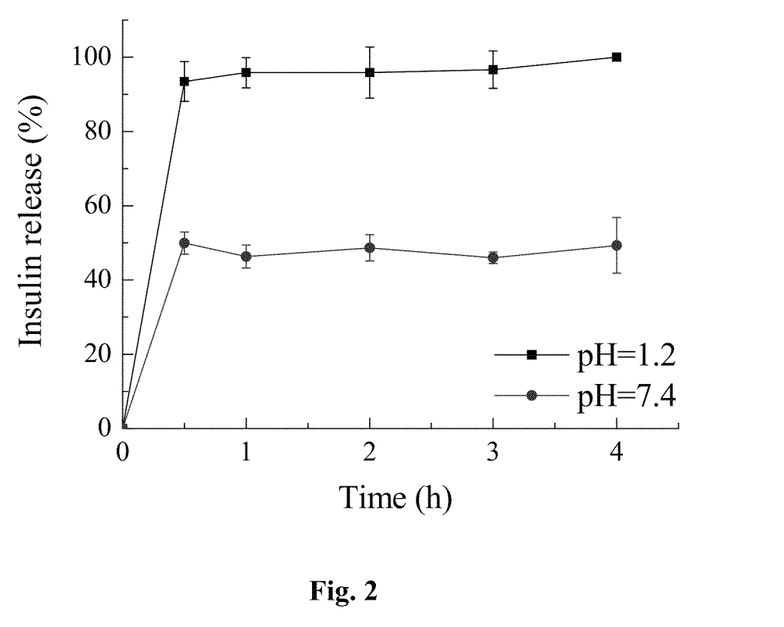
FIG. 2 shows a representative in vitro study with insulin drug release profile of cationic nanoparticles without capsule in the simulated gastrointestinal mediums.

The in vitro insulin release profiles from the PLGA/RS nanoparticles with and without HP55-coated capsule are evaluated at acidic and alkaline pH environments. As shown in FIG. 2, PLGA/RS nanoparticles without HP55-coated capsule display an unfavorable pH-sensitive release profile. More than 90% of insulin is released at pH 1.2 medium within the first 1 h, while 50% of insulin is released within 1 h at pH 7.4 medium. Insulin release from PLGA/RS nanoparticles may be modulated by a swelling-diffusion process. At lower pH, RS polymers repel to each other due to repulsive electrostatic interactions, resulting in a swelling and permeable polymer matrix. As such, insulin (PI=5.4) becomes positively charged molecule at pH 1.2, and creates repulsively electrostatic interactions with the positively charged RS polymer, resulting in promoting release of insulin. In contrast, insulin is mainly negatively charged in the intestinal medium, leading to electrostatic interactions with the positively charged polycationic polymer. Thus, the incomplete release of insulin from PLGA/RS nanoparticles in pH 7.4 condition (e.g. PBS) is due to the part of insulin retained and absorbed in the nanoparticles by electrostatic interactions.

Figure 3:
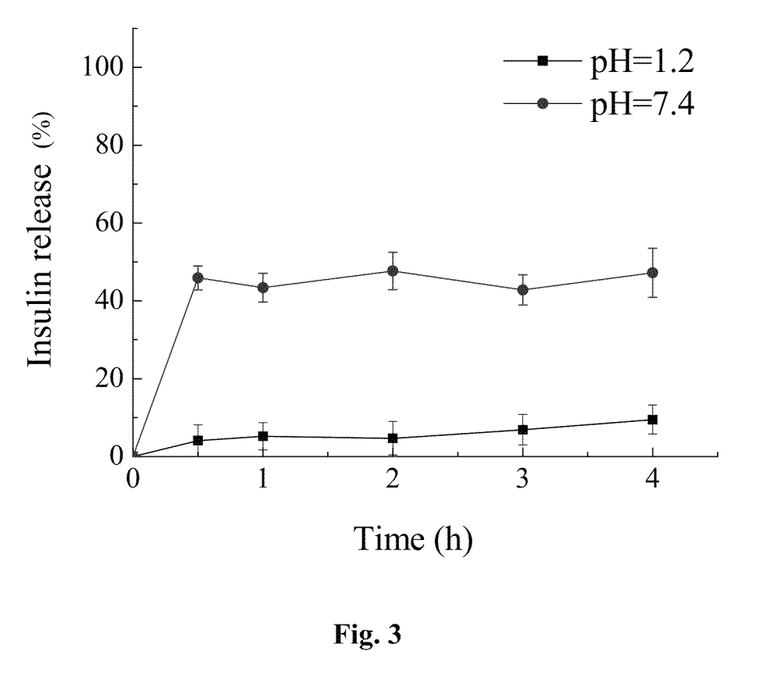
FIG. 3 shows a representative in vitro study with insulin drug release profile of cationic nanoparticles with capsule in the simulated gastrointestinal mediums.

As shown in FIG. 3, in the case of HP55-coated capsule filled with PLGA/RS nanoparticles, nanoparticles are almost retained in the capsule and the initial release of insulin is dramatically reduced in the pH 1.2. The release of insulin from PLGA/RS nanoparticles which are contained in the capsule at pH 7.4 is similar to that from PLGA/RS nanoparticles directly, indicating that the HP55-coated capsule has no influence on the release of insulin from the nanoparticles in the physiological environment of the intestine in a subject to whom the enteric-coated capsule of the present invention is orally administered.

Example 5

Figure 4:
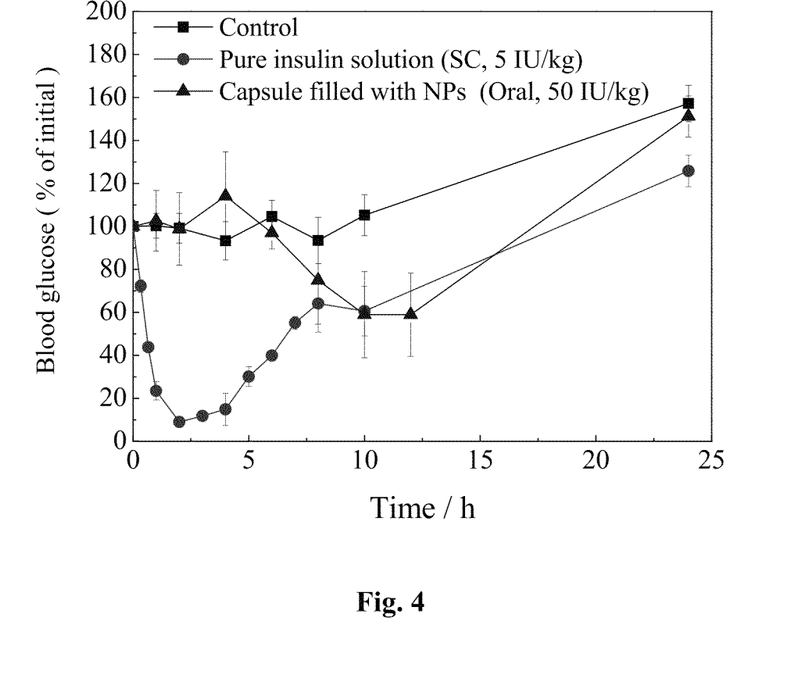
FIG. 4 shows the effect of orally administrated insulin-loaded cationic nanoparticles on 'glucose reduction %' in diabetic rats.

In Vivo Study with Enteric-Coated Capsule Containing Cationic Nanoparticles after Oral Administration in Diabetic Rats FIG. 4 shows the blood glucose level-time profiles after administration of the insulin PLGA/RS nanoparticles with capsule to diabetic rats. The effect of insulin-loaded nanoparticles on the blood glucose levels is shown by comparing with that of the S.C. injection of insulin. As expected, no hypoglycemic effect was observed in the untreated control group, indicating a stable diabetic level in the STZ-induced animals.

TABLE 4

| Forms | $AAC_{0-24h}$ (% h) | Hypo-glycemic Effect (%) | PA (%) | $T_{max}$ (h) | $C_{min}$ (%) |
|---|---|---|---|---|---|
| Enteric-coated capsule (oral) | 931 | 32.9 | 9.2 | 10 | 58.9 ± 20 |
| Insulin free-form (SC) | 1008 | 35.2 | 100 | 2 | 11.72 ± 1.1 |

Data represents the mean ± SD,
n = 3 per group
$T_{max}$ = time at minimum relative basal glucose concentration in the blood
$C_{min}$ = minimum relative basal glucose concentration in the blood As shown in FIG. 4, both oral administration of capsule filled with PLGA/RS nanoparticles (NP) and subcutaneous (SC) injection of insulin solution show a significant hypoglycemic effect in the diabetic rats. SC injection of the insulin solution produces a sharp decrease in blood glucose level (90% in 2 h), which gradually returns to the basal level at 10 h, whereas the hypoglycemia effect is less significant after oral administration of the enteric-coated capsules which produces a slower but prolonged reduction in blood glucose level. The blood glucose level of the diabetic rats increases slightly during the first 4 hours of the experiment, possibly due to physical stress during handling and blood sampling. The hypoglycemic effect and the pharmacological availability (PA) of the enteric-coated capsule, determined by the dose-corrected $AAC_{0-24h}$ over 24 h relative to SC free-form insulin, as noted in Table 4, are 32.9% and 9.2%, respectively.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions

What we claim:

1. A composition comprising an enteric-coated capsule enclosing a plurality of nanoparticles and a solubilizer, wherein each of said plurality of nanoparticles further comprises a polycationic polymer, a biodegradable polymer that is a copolymer which is degradable by hydrolysis following exposure to physiological environment of human intestine, a bioactive substance and a stabilizer; said solubilizer is trehalose in a concentration of 1.5% w/w or w/v.

2. The composition of claim 1, wherein the polycationic polymer is a copolymer of acrylic and methacrylic acid esters with quaternary ammonium cations having a molecular weight from 150 to 200 kDa.

3. The composition of claim 1, wherein the biodegradable polymer is poly(lactic acid-co-glycolic acid) having a molecular weight from 20 to 40 kDa.

4. The composition of claim 1, wherein the enteric-coated capsule further comprises a hard gelatin capsule and a pH-sensitive coating layer which is coated on the surface of said hard gelatin capsule in order to form said enteric-coated capsule, said pH-sensitive coating layer being composed of a polymer which is selected from the group consisting of hydroxypropylmethylcellulose phthalate, hydroxypropylmethylcellulose acetate succinate, ethyl acrylate and methyl methacrylate.

5. The composition of claim 1, wherein the stabilizer is a polyvinyl alcohol.

6. The composition of claim 1, wherein said bioactive substance is encapsulated in each of said plurality of nanoparticles; said plurality of nanoparticles are further encapsulated in said enteric-coated capsule.

7. The composition of claim 1, wherein said bioactive substance is insulin.

8. The composition of claim 1, wherein said nanoparticles are mucoadhesive when surrounding medium is at a pH between 6.0 and 7.4 which is similar to the pH of an intestinal medium.

9. The composition of claim 1 is administered orally to a subject in needs thereof, wherein the bioactive substance is released from said nanoparticles to the upper region of the small intestine of the subject with a controlled release profile of $T_{max}$ at about 10 hours and $C_{min}$ at about 58.9%.

10. The composition of claim 7, wherein said insulin is selected from the group consisting of regular insulin and insulin analogs.

11. A method of preparing cationic nanoparticles of claim 1, comprising:
    (a) forming a double emulsions comprising an insulin solution, a polycationic polymer, a biodegradable polymer, a stabilizer and an organic solvent;
    (b) forming insulin-loaded nanoparticles by evaporation of the organic solvent from said double emulsions;
    (c) forming purified insulin-loaded nanoparticles by centrifugation and washing the nanoparticles for three times; and
    (d) forming the cationic nanoparticles by freeze-drying the purified insulin-loaded nanoparticles overnight.

12. The method of claim 11, wherein each of the nanoparticles has a mean particle size about 250-300 nanometers.

13. The method of claim 11, wherein the insulin solution contains an insulin molecule selected from the group consisting of regular insulin and insulin analog.

14. The method of claim 11, wherein the polycationic polymer is a copolymer of acrylic and methacrylic acid esters with quaternary ammonium cations having a molecular weight from 150 to 200 kDa.

15. The method of claim 11, wherein the biodegradable polymer is poly(lactic acid-co-glycolic acid) having a molecular weight from 20 to 40 kDa.

16. The method of claim 11, wherein the stabilizer is a polyvinyl alcohol.

17. The method of claim 11 further comprising:
    (a) filling a hard gelatin capsule with the cationic nanoparticles; and
    (b) forming an enteric-coated capsule by coating a pH-sensitive coating polymer on the surface of the hard gelatin capsule.

* * * * *